United States Patent
Krüger et al.

(10) Patent No.: US 11,337,661 B2
(45) Date of Patent: May 24, 2022

(54) MEDICAL NAVIGATION SYSTEM WITH WIRELESSLY CONNECTED, TOUCH-SENSITIVE SCREEN

(71) Applicant: Intersect ENT GmbH, Hennigsdorf (DE)

(72) Inventors: Timo Krüger, Berlin (DE); Dirk Mucha, Glienicke/Nordbahn (DE); Andreas Rose, Oberkramer (DE); Hannes Braun, Graz (AT)

(73) Assignee: Intersect ENT GmbH, Hennigsdorf (DE)

( * ) Notice: Subject to any disclaimer, the term of this patent is extended or adjusted under 35 U.S.C. 154(b) by 976 days.

(21) Appl. No.: 14/387,722

(22) PCT Filed: Mar. 28, 2013

(86) PCT No.: PCT/EP2013/056802
§ 371 (c)(1),
(2) Date: Sep. 24, 2014

(87) PCT Pub. No.: WO2013/144334
PCT Pub. Date: Oct. 3, 2013

(65) Prior Publication Data
US 2015/0087968 A1 Mar. 26, 2015

(30) Foreign Application Priority Data
Mar. 29, 2012 (DE) .................... 10 2012 205 165.1

(51) Int. Cl.
*A61B 6/12* (2006.01)
*A61B 34/20* (2016.01)
(Continued)

(52) U.S. Cl.
CPC ............... *A61B 6/12* (2013.01); *A61B 5/055* (2013.01); *A61B 6/032* (2013.01); *A61B 34/20* (2016.02);
(Continued)

(58) Field of Classification Search
CPC ..................................................... A61B 90/37
See application file for complete search history.

(56) References Cited

U.S. PATENT DOCUMENTS

| | | |
|---|---|---|
| 2004/0169673 A1 | 9/2004 | Crampe et al. |
| 2004/0263535 A1 | 12/2004 | Birkenbach |

(Continued)

FOREIGN PATENT DOCUMENTS

| | | |
|---|---|---|
| DE | 202 20 584 U1 | 4/2004 |
| DE | 10 2006 003 610 A1 | 8/2007 |

(Continued)

OTHER PUBLICATIONS

Alex Olwal; "Hybridsurface: Multi-user, multi-device, remote collaboration"; Vimeo; https://vimeo.com/30581634; 2009; screen shots of video at five second intervals; entire video.

(Continued)

*Primary Examiner* — Shahdeep Mohammed
(74) *Attorney, Agent, or Firm* — Cooley LLP (57) ABSTRACT

A medical system comprises an instrument, a position acquisition apparatus, a data processing and image generating apparatus and an image display and control unit. The position acquisition apparatus is configured to acquire a position and orientation of the instrument in relation to a reference coordinate system. The data processing and image generating apparatus is configured to generate an image of a body part from currently recorded or stored data representing a body part, which image reproduces a view of the body part together with a representation of the position, and preferably (Continued)

also the orientation of the instrument so that an observer can gather the position and orientation of the instrument in the body part from the image of the body part.

19 Claims, 4 Drawing Sheets

(51) Int. Cl.
    *A61B 34/00*     (2016.01)
    *A61B 5/055*     (2006.01)
    *A61B 6/03*     (2006.01)
    *G06F 3/0482*     (2013.01)
    *G06F 3/04842*     (2022.01)
    *G06F 3/04847*     (2022.01)
    *A61B 34/10*     (2016.01)
    *A61B 90/00*     (2016.01)

(52) U.S. Cl.
    CPC ............ *A61B 34/25* (2016.02); *G06F 3/0482* (2013.01); *G06F 3/04842* (2013.01); *G06F 3/04847* (2013.01); *A61B 90/37* (2016.02); *A61B 2034/102* (2016.02); *A61B 2034/2051* (2016.02); *A61B 2034/2063* (2016.02); *A61B 2034/2074* (2016.02); *A61B 2034/258* (2016.02); *A61B 2090/374* (2016.02); *A61B 2090/3762* (2016.02)

(56) References Cited

U.S. PATENT DOCUMENTS

| | | |
|---|---|---|
| 2005/0020909 A1 | 1/2005 | Moctezuma de la Barrera et al. |
| 2006/0264749 A1* | 11/2006 | Weiner .................. A61B 6/032 600/437 |
| 2007/0034731 A1* | 2/2007 | Falco ..................... G01B 7/008 244/3.1 |
| 2007/0070194 A1* | 3/2007 | Abe ................... A61B 1/00016 348/72 |
| 2007/0111726 A1* | 5/2007 | Lambert ........... H04M 1/72563 455/432.1 |
| 2008/0077158 A1 | 3/2008 | Haider et al. |
| 2009/0228813 A1 | 9/2009 | Sekiguchi |
| 2011/0015523 A1* | 1/2011 | Sabata ..................... A61B 8/12 600/443 |
| 2011/0118557 A1* | 5/2011 | McKenna .............. G16H 40/63 600/300 |
| 2011/0137156 A1 | 6/2011 | Razzaque et al. |
| 2011/0178389 A1* | 7/2011 | Kumar ...................... G06T 7/33 600/411 |
| 2015/0182297 A1* | 7/2015 | Sandhu .................... A61B 6/12 600/424 |

FOREIGN PATENT DOCUMENTS

| | | |
|---|---|---|
| EP | 1 915 962 A1 | 4/2008 |
| EP | 2 179 703 A1 | 4/2010 |
| WO | 2010/123858 A2 | 10/2010 |

OTHER PUBLICATIONS

Alex Olwal, et al; "Design and Evaluation of Interaction Technology for Medical Team Meetings"; Interact 2011, Part 1; IFIP International Federation for Information Processing 2011; 2011; pp. 505-522.

International Search Report dated Jul. 12, 2013, for PCT Application No. PCT/EP2013/056802, filed on Mar. 28, 2013, 3 pages.

Written Opinion of the International Searching Authority dated Jul. 12, 2013, for PCT Application No. PCT/EP2013/056802, filed on Mar. 28, 2013, 9 pages.

* cited by examiner

MEDICAL NAVIGATION SYSTEM WITH WIRELESSLY CONNECTED, TOUCH-SENSITIVE SCREEN

CROSS REFERENCE TO RELATED APPLICATIONS

This application is the U.S. National Stage of International Application Number PCT/EP2013/056802 filed on Mar. 28, 2013, which application claims priority under 35 USC § 119 to German Patent Application No. 10 2012 205165.1 filed on Mar. 29, 2012 Both applications are hereby incorporated by reference in their entirety.

TECHNICAL FIELD

The invention relates to a medical system comprising an instrument, a position acquisition apparatus for the instrument and a data processing and image generating apparatus.

BACKGROUND OF THE INVENTION

Using such a medical system, it is possible, for example, to acquire the position and orientation of a medical instrument, and the position data acquired thus can, for example, be assigned to a tomographic image of an object or body part. The data processing and image generating apparatus is then able to generate an image of a body part from currently recorded or stored data representing a respective body part, which image reproduces a view of the body part together with a representation of the position and orientation of the instrument in such a way that an observer can gather the position and orientation of the instrument in the body part from the image of the body part. The position data, recorded for this purpose by the position acquisition apparatus, typically reproduce a position and orientation of a respective instrument in relation to a reference coordinate system and can therefore be transformed into a coordinate system underlying the image data by the data processing and image generating apparatus. In principle, such medical systems are known and serve for so-called navigation of surgical instruments, which are typically guided by hand. Therefore, an operator is able also to identify the position of the instrument guided by him in a reproduction, for example a tomographic reproduction, of his patient and is therefore able to guide the instrument to a target region or a target position in a targeted manner. By way of example, the employed position acquisition systems can be optical, ultrasound-based or electromagnetic position acquisition apparatuses. By way of example, electromagnetic position acquisition apparatuses are known, in which a field generator generates an alternating electromagnetic field and position sensors comprising coils are provided on the instrument. Currents which depend on the alignment of a respective coil in relation to the alternating electromagnetic field are induced in the coils by the alternating electromagnetic field of the generator. If a movable instrument is equipped with such position sensors in the form of sensor coils, it is possible to determine a location and position of the instrument relative to a reference sensor, which e.g. may likewise comprise coils. Here, the reference sensor, for example as a patient localizer, is securely connected to a body part of a patient (or else of a different object).

For navigation in body parts of a patient, the position and orientation of an instrument is typically acquired using such a position acquisition apparatus and the position of the instrument is subsequently displayed in slice images of the body part obtained by tomography. In order for this to work, the position data supplied by the position sensor of the instrument must be transformed into coordinates of the tomographic image of the patient. The position of the instrument, and preferably the orientation thereof as well, can then be depicted in slice images, or else perspective representations, of the body part of a patient.

It is helpful to the operator if, for this, he is able to select the representation most expedient in each case; if, for example, he is able to select different slice planes in order to be able in each case to select a representation that is useful to him. Therefore, provision is made for equipping such position acquisition apparatuses or data processing and image generating apparatuses with input means which, for example, allow the selection of a display format.

The invention is based on the object of improving such a system, especially in view of the operability by the operator.

SUMMARY OF THE INVENTION

According to the invention, this object is achieved by a medical system comprising an instrument, a data processing and image generating apparatus and an image display and control unit. Of these, the position acquisition apparatus is configured to acquire a position and orientation of the instrument in relation to a reference coordinate system. The data processing and image generating apparatus is configured to generate an image of a body part from currently recorded or stored data representing a body part, which image reproduces a view of the body part together with a representation of the position, and preferably also the orientation, of the instrument in such a way that an observer can gather the position and orientation of the instrument in the body part from the image of the body part. Here, according to the invention, the image display and control unit is wirelessly connected to the data processing and image generating apparatus, and comprises a display and input unit with a closed surface. On the closed surface of the display and input unit, control elements and a respective view of the body part are displayed during operation of the image display and control unit, together with a representation of the position, and preferably also the orientation, of the instrument. The image display and control unit is configured to accept user inputs via displayed control elements and to transmit control signals to the data processing and image generating apparatus as a function of the respectively accepted user inputs.

By way of example, the display and input unit can be a touchscreen, i.e. a touch-sensitive screen, which also permits inputs via the screen. The display and input unit can also easily be used in an operating theater as a result of such a display and input unit being closed, as it is not so susceptible to contamination.

Since the image display and control unit is moreover connected wirelessly to the data processing and image generating apparatus, the image display and control unit can be placed or installed at in each case the most expedient location by the operator, or else it can be operated hands-free. Thus, the operator can enter control inputs directly from the operation site or directly compare images on the image display and control unit with what is in front of his eyes in the case of a patient.

In order to simplify the last aspect in particular, the medical system is preferably configured in such a way that the display and control unit displays a respective view of a body part with a 1:1 scale such that distances in a depicted slice plane of a body part are at least approximately identical to a distance along the slice plane in the body part itself. This not only permits a comparison between what the operator has in front of his eyes in the case of the patient and corresponding images, it also allows the operator to guide his instrument particularly precisely since the distances to be gathered from the image display on the display and control unit precisely correspond to those by which he may, optionally, need to move the instrument in order, for example, to arrive at a specific target position.

In this context it is particularly preferable for the data processing and image generating apparatus to be furthermore configured to display in a respective view of a body part in addition to a respective position also preferably an orientation of the instrument as well as a marking of a further position and/or of a target region or target volume in the body part.

Preferably, the data processing and image generating apparatus is configured to access different data representing a respective body part, for example data obtained by computed tomography or data obtained by magnetic resonance imaging. Moreover, the data processing and image generating apparatus is accordingly configured to generate an image, as desired, which image is based on data obtained by computed tomography or data obtained by magnetic resonance imaging. In this context, the image display and control unit is preferably configured to display one or more control elements, which serve for the selection to be made between various data representing a respective body part and, hence, the corresponding image display. The image display and control unit is configured to generate a control signal when an appropriate control element is actuated, which control signal causes the data processing and image generating apparatus to generate an image on the basis of the correspondingly selected data representing a body part of the patient.

Moreover, the data processing and image generating apparatus is preferably configured to store a displayed image in such a way that it can be recalled at a later time. This is therefore advantageous because, typically, the position of the instrument in the body part, and possibly the body part as well, change or move over time such that, typically, a currently reproduced image differs from an image reproduced at an earlier time. Therefore, it may be helpful to store an image at specific times, for example within the meaning of a screenshot. In this respect, the image display and control unit also preferably comprises a corresponding control element, wherein the image display and control unit generates a control signal when said control element is actuated, which control signal causes the data processing and image generating apparatus to store a respectively currently displayed image when the control element is actuated.

Similarly, it may be desirable for the data processing and image generating apparatus to be configured to store an image sequence in the style of a film. In order to trigger this, the image display and control unit also preferably comprises a corresponding control element, wherein the image display and control unit generates a control signal when said control element is actuated, which control signal causes the data processing and image generating apparatus to record an image sequence within the meaning of a film.

In accordance with a particularly preferred embodiment variant, the display of the control element for triggering the recording of an image sequence is modified in the case of the actuation which starts the recording of an image sequence. Thus, on the basis of the display of the control element, the operator can himself identify that an image sequence is currently being recorded. The image display and control apparatus is furthermore preferably configured for a second actuation of the control element for recording image sequences to again stop the recording of a respective image sequence. Preferably, the image display and control unit once again generates the original display of this control element prior to triggering the recording of an image sequence in the case of the respective second actuation of the control element.

BRIEF DESCRIPTION OF THE DRAWINGS

The invention is now intended to be explained in more detail on the basis of an exemplary embodiment, with reference being made to the figures. In detail.

DETAILED DESCRIPTION

Figure 1:
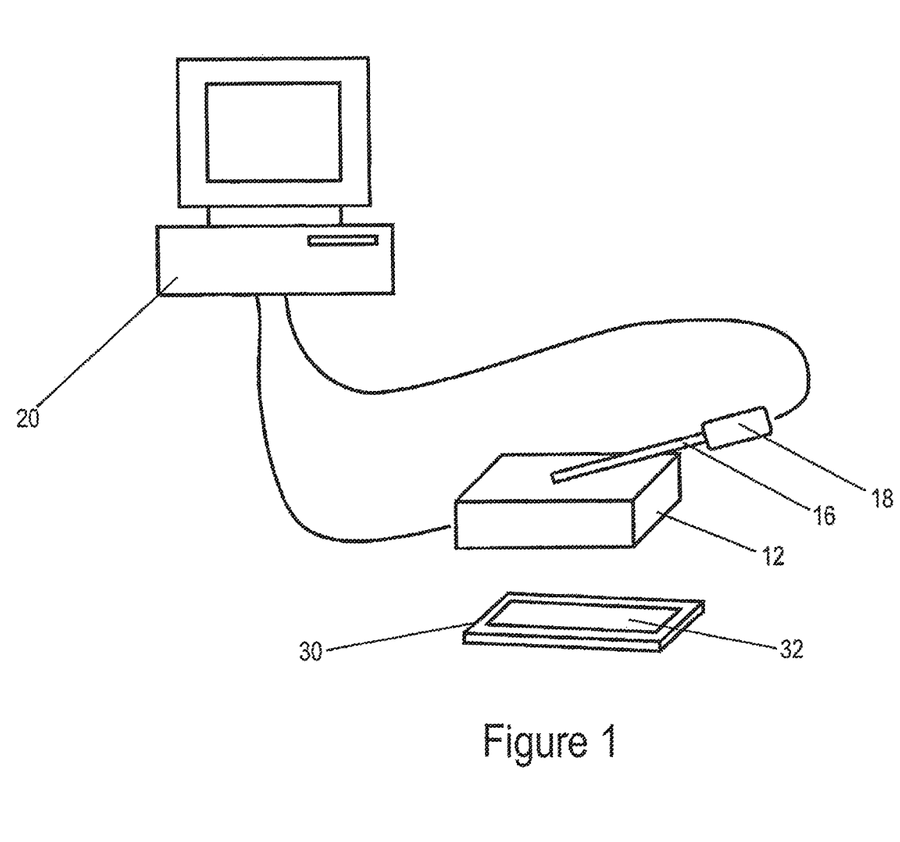
FIG. 1 shows a medical system comprising an instrument, a position acquisition apparatus for this instrument, a data processing and image generating apparatus and an image display and, control unit.

FIG. 1 shows the components of a medical system, specifically an instrument 16, a field generator 12 as part of a position acquisition apparatus and a data processing and image generating apparatus 20, which is connected to the field generator 12 and the instrument 16 via cables 22 and 24, respectively. Moreover, FIG. 1 shows an image display and control unit 30, which can easily be held by one or two hands and is wirelessly connected to the data processing and image generating apparatus 20.

Figure 2:
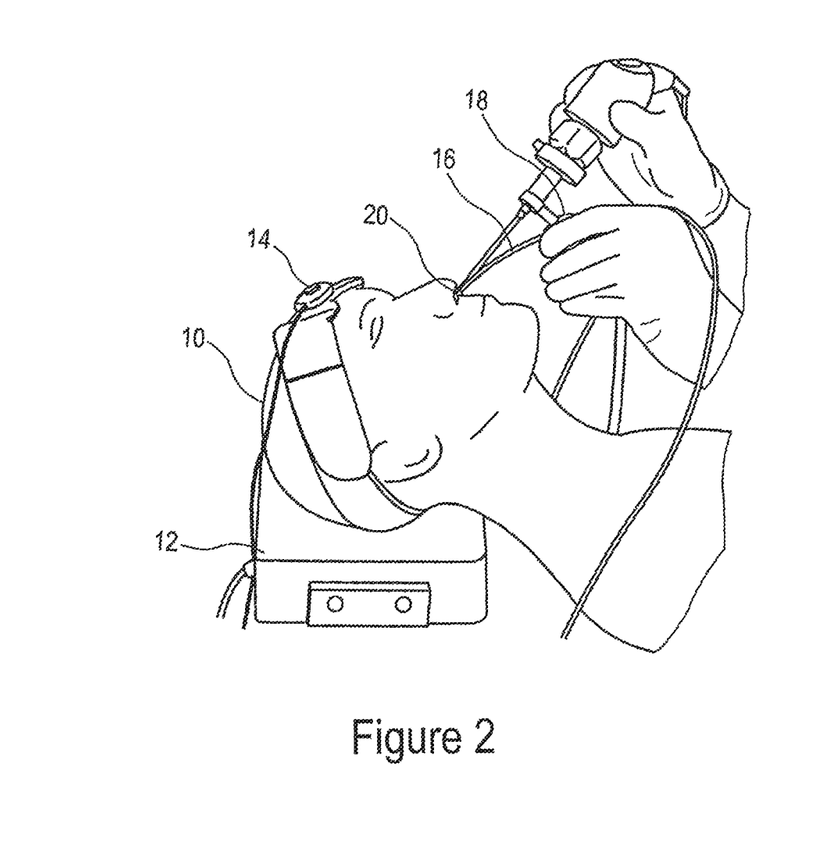
FIG. 2 shows a medical instrument and an associated position acquisition apparatus comprising a field generator for an alternating electromagnetic field, and a position sensor fixed with respect to the patient.

FIG. 2 shows, by way of a sketch, the head 10 of a patient in a side view. The field generator 12 for generating an alternating electromagnetic field, which is to be acquired in the region of the head of the patient, is situated in the vicinity of the head 10. A position sensor, which is fixed with respect to the patient, representing a reference position sensor 14 or patient localizer is fastened to the head 10 of the patient. The movable instrument 16 comprises a proximal end with a handle 18 and a distal end with an instrument position sensor. The reference position sensor 14 and the instrument position sensor respectively comprise one or more electrical coils as sensor coils. The alternating electromagnetic field emanating from the field generator 12 during operation respectively induces a current in the coils, the amplitude of which current depends on the relative position and alignment of a respective sensor coil in relation to the field generator 12. Thus, it is possible, in a manner known per se, to determine the relative position and alignment (orientation) of the instrument position sensor in relation to the reference position sensor.

In order to use position values of an instrument, acquired by means of a position acquisition system, for instrument navigation within the meaning of a respectively current position of an instrument being displayed in slice images of a body part obtained e.g. by tomography, the position values supplied by the position sensor of the instrument must be transformed into a model coordinate system underlying a tomographic image. A transformation prescription required for this is obtained in a manner known per se by means of a registration method. By way of example, a surface of a body part is, to this end, scanned by means of a pointing or scanning instrument, and position values obtained in the process are transferred with the smallest possible error to a model surface derived from a tomogragphic or topographic image. The scalings, rotations and/or translations or the like, which are required for this transfer which is as accurate as possible, finally result in the transformation prescription.

The data processing and image generating apparatus 20 can also be at a distance from the operation site, for example as part of a central data center.

The instrument 16 may be a surgical instrument or a microscope, endoscope or different movable instrument. The instrument 16 need not necessarily be movable by hand, but may also be controlled by a robot. The image display and control unit 30 is configured as an independent unit, which communicates wirelessly at least with the data processing and image generating apparatus 20, but can, for example, additionally also communicate with the instrument 16 in order to be able to control, in particular, the instrument 16 remotely by means of the image display and control unit 30. By way of example, if the instrument 16 is an endoscope, the alignment of the endoscope optical unit can be controlled by means of the image display and control unit 30 to the extent that said optical unit can be aligned by remote control. If the instrument 16 is a microscope, the display and control unit 30 can be configured to control the focus control of the microscope or the overriding or setting of the autofocus control of the microscope remotely.

Figure 3:
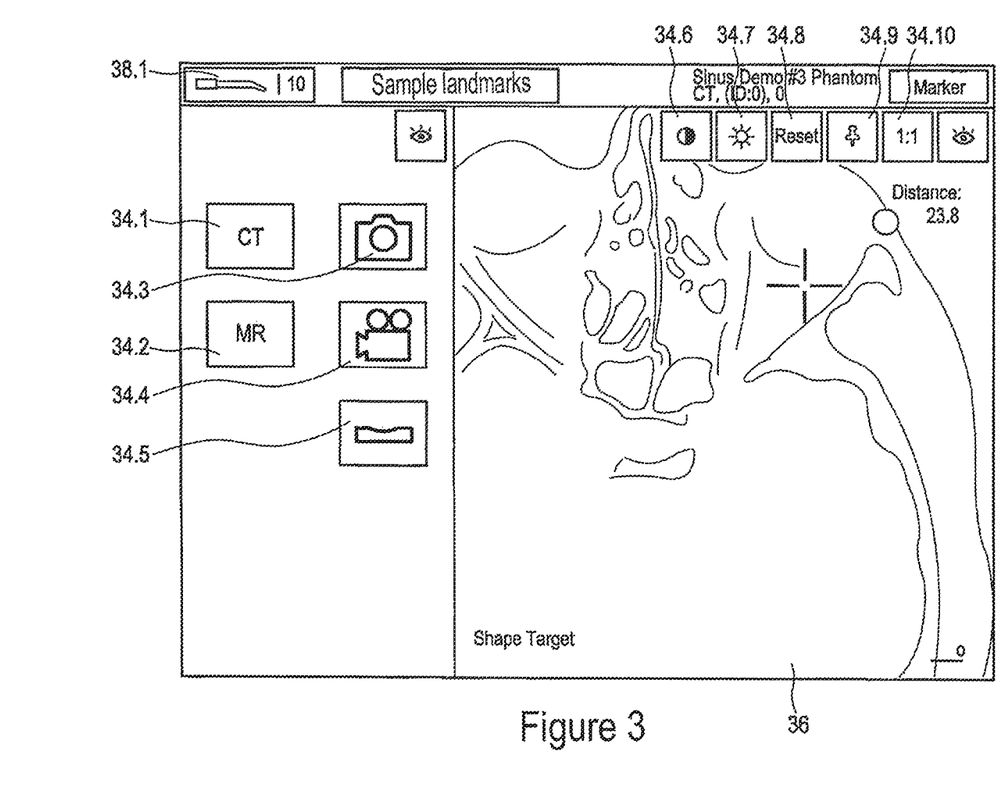
FIG. 3 shows an example of an image generated by the data processing and image generating apparatus and displayed on the image display and control unit, together with control elements likewise displayed on the image display and control unit.

As can be gathered from FIG. 3, the display and input unit 32 of the image display and control unit 30 displays both at least one view 36 of a body part and one or more control elements 34, and also information icons 38. As already described above, the view 36 of a body part can be generated by data of a body part obtained from the data processing and image generating unit 20 by way of e.g. computed tomography or magnetic resonance imaging. Additionally or alternatively, the depicted view can also be a respectively current endoscope or microscope recording. Preferably, both views displayed from data obtained by tomography and views recorded by means of an optical instrument, such as an endoscope or a microscope, are displayed simultaneously. The view of a respective body part is preferably displayed with a scale of 1:1 such that distances on the plane of the display and input unit 32 of the image display and control unit 30 correspond to distances in the respective plane of the body part.

Both the position of a respective instrument 16 and also e.g. planning information, which is a result of preceding operation planning, are preferably displayed in the respective views of a body part. By way of example, such planning information can be the marking of a target region or a target volume in the respectively depicted view 36 of the body part. Other planning information can relate to the position and alignment of implants such as e.g. screws. If these are depicted in the view 36 of the body part, an operator can precisely align the real implant during the operation on the basis of the depicted planning information in the view 36 of the body part.

Figure 4:
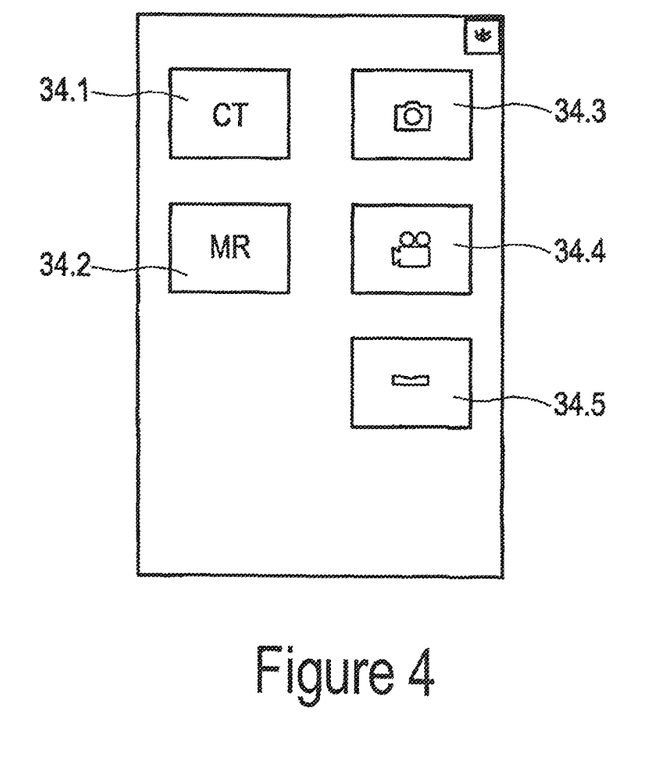
FIG. 4 shows a display of control elements displayed on the image display and control unit.

Control elements 34 depicted on the display and input unit 32 can be gathered from FIGS. 3 and 4 in an exemplary manner. By way of example, a first control element 34.1 and a second control element 34.2 serve for selecting the data representing a respective body part.

Thus, by actuating the first control element 34.1, a user can cause the view 36 of the body part from data obtained by computed tomography to be displayed. By actuating the second control element 34.2, a user can cause the view 36 to be generated from data obtained by magnetic resonance imaging. In each case, actuating a respective control element 34.1 or 34.2 triggers the transmission of a corresponding control signal from the image display and control unit 30 to the data processing and image generating unit. The latter then generates corresponding views 36 of the body part and transmits these to the image display and control unit 30, on the display and input unit 32 of which the corresponding view 36 is then depicted.

A third control element 34.3 enables snapshots to be recorded, either of a respectively current view 36 of the body part only or else of the whole display, including the control elements, depicted on the display and input unit 32. If the third control element 34.3 is actuated by a user, the image display and control unit 30 generates a control signal which prompts the data processing and image generating apparatus 20 to store a corresponding view in such a way that it can be recalled at a later time.

Similarly, a fourth control element 34.4 enables the recording of an image sequence to be triggered, which, in the style of a film, is stored either on the image display and control unit 30 itself or else on the data processing and image generating apparatus 20. The recording of such an image sequence is started with a respective first actuation of the fourth control element 34.4, while pressing the fourth control element 34.4 a second time stops the recording of the image sequence again. The display of the fourth control element 34.4 is modified after the first actuation thereof such that a user immediately knows that an image sequence is currently being recorded. If this recording of an image sequence is stopped again by a respective second actuation of the fourth control element 34.4, the fourth control element 34.4 is once again depicted in its original display format shown in FIGS. 3 and 4.

Further control elements 34.6 and 34.7 serve, for example, for setting the contrast (control element 34.6) and brightness (control element 34.7) of the displayed view.

An eighth control element enables a reset. By actuating the eighth control element 34.8, the original settings are restored.

Using a ninth control element 34.9, positions can be marked in the depicted view 36 of the body part. A tenth control element 34.10 enables switching between different display scales, wherein a display scale of 1:1 is preferred.

Moreover, the image display and control unit 30 allows switching between various instruments that are connected wirelessly to the image display and control unit 30, for example switching between endoscope and surgical instrument.

However, switching between various instruments can also be brought about automatically by an operator picking up a respective instrument. In this case, the respective instrument currently in use is displayed on the display and input unit 32 by an information icon such as the icon 38.1.

From the interaction between the image display and control unit 30 and an instrument 16 in the form of an endoscope, a particularly advantageous application emerges to the extent that, for example, the attention can be focused on image points or positions, determined by the endoscope, in a two-dimensional plane or in a three-dimensional space (i.e., for example, these can be brought into the center of the endoscope image). A respective position can be stored by actuating a corresponding control element, either on the display and input unit 32 of the image display and control unit 30 or else on the endoscope itself. A plurality of such positions can subsequently be connected to one another in a polygonal train which, for example, describes a body cavity or else a cavity—more precisely: the contour thereof— artificially created by an operation (e.g. after removing a tumor). Such a polygonal train can then serve as a template for cutting out body tissue parts, which for example should serve for filling the artificially created cavity and are taken from a different position of the body of a patient.

Instead of generating a polygonal train from individual body positions driven to by means of the endoscope, provision can also be made for continuous tracking of the alignment, of the endoscope in order thus to generate a continuously recorded template. However, incorrect alignments of the endoscope while recording the template would also be recorded in the process.

Moreover, the image display and control unit 30 itself also allows a user to mark individual positions or else trace out depicted contours on the view 36 of a body part, for example by means of an input stylus, in order thus to generate the corresponding position data for generating a template.

A further function offered by the image display and control unit 30 lies in the sensing of landmarks on the view 36 of the body part in order thus, for example, to bring various displays, such as e.g. an endoscopic recording and a view generated from data obtained by tomography, in line, to corresponding landmarks are assigned to one another in the various representations.

Provision can also be made for the image display and control unit 30 to be able to be connected to various instruments and/or data processing and image generating apparatuses 20 such that a plurality of operations can be tracked by means of a single image display and control unit 30 by switching between different data processing and image generating apparatuses 20.

Basic settings for various users of an image display and control unit 30 and/or basic settings for various image display and control units 30 can be stored either on a respective image display and control unit 30 or else on a corresponding data processing and image generating apparatus 20, in particular if the latter is implemented in the form of a central server or data center. This renders it possible, particularly on a central data processing and image generating apparatus 20 as well, to store basic settings for various users such that respectively different image display and control units 30, even with different operating systems, can be used without a user having to adapt himself to in each case very different representation manners or pre-settings. Rather, the representation manners and pre-settings can respectively be realized to be the same, or at least similar, on various image display and control units, independently of a respectively specific image display and control unit 30 and the specific operating systems thereof.

Moreover, it is possible for data to be stored in a respective image display and control unit 30, which data either partly or completely describe a respective medical system. These can include instrument descriptions, as well as descriptions of the position acquisition apparatus or else of the data processing and image generating apparatus. Such data can be stored permanently in a respective image display and control unit 30, or else can only be transmitted with the start of a respective application, for example from a corresponding data processing and image generating apparatus 20 to a respective image display and control unit 30. In the latter case, different image display and control units 30 of different types or with different equipment can also, in particular, easily be replaced for one another.

Conversely, data which describe individual image display and control units 30, optionally also individually for different users of a respective image display and control unit 30, can also be stored in a respective data processing and image generating apparatus 20.

In one extreme case, the complete data processing and image generating apparatus 20 can also be integrated in a respective image display and control unit 30.

Conversely, it is also possible for all essential information to be stored in the data processing and image generating apparatus 20 such that, firstly, the image display and control unit 30 can be kept quite simple and, secondly, all essential information is kept available centrally and therefore kept available for other users or image display and control units 30 as well. By way of example, if the whole representation on a respective display and input unit 32 of an image display and control unit 30, including the positions and display formats of the control elements, is predetermined by a corresponding data processing and image generating apparatus 20, it may be sufficient for a respective image display and control unit 30 only to generate one control signal when a corresponding, depicted control element on the display and input unit 32 is touched, which control signal reflects the respectively touched position on the display and input unit 32. This information is then sufficient for the data processing and image generating apparatus 20 to identify which control element was actuated on the image display and control unit 30 or which position was marked on the displayed view 36 of a body part.

By virtue of, thus, all essential functionalities of the image display and control unit 30 being in fact provided and executed by the data processing and image generating apparatus 20, it is possible to provide simultaneous powerful functionalities and provide simple, in particular small and light, image display and control units 30. Since, as explained above, the data processing and image generating apparatus 20 also need not be in the direct vicinity of a user or operator, but may for example be realized in a central data center, a user or operator can, within his work surroundings, concentrate fully on his instruments and optionally resort to the image display and control unit 30 for support. Since the latter optionally may also serve as remote control for the corresponding instruments of the user or operator (see above), this greatly simplifies the work of the user and operator at his workplace—for example in the operating theater.

In particular, an image display and control unit 30 described here permits instrument-centered work of the user or operator, during which the latter can wholly concentrate on his instruments and is largely unburdened from further technical burdens.

LIST OF REFERENCE SIGNS

10 Patient head
12 Field generator
14 Position sensor fixed with respect to the patient
16 Movable instrument
18 Handle of the movable instrument
20 Data processing and image generating apparatus
22 Connecting cable
24 Instrument cable
30 Image display and control unit
32 Display and input, unit
34 Control element 36 View of a body part
38 Information icon

The invention claimed is:

1. A medical system comprising:
an instrument;
an electromagnetic position acquisition apparatus for the instrument configured to acquire
a position of the instrument in relation to a reference coordinate system;
a computer configured to generate an image of a body part from currently recorded or stored data representing the body part, wherein the image reproduces a view of the body part together with a representation of the position of the instrument such that an observer can determine the position of the instrument in the body part from the image of the body part; and
a user interface device selectable from a plurality of different user interface devices as being the user interface device of the medical system,
wherein the user interface device is wirelessly connected to the computer and comprises a closed display on which one or more control elements are displayed, and on which the view of the body part and the representation of the position of the instrument are displayed during operation, wherein the user interface device is configured to accept user inputs via the displayed one or more control elements and to transmit control signals to the computer as a function of the accepted user inputs,
wherein basic settings relating to representation manners for any one of the plurality of different user interface devices are stored either on one or more of the plurality of different user interface devices or on the computer, and wherein the basic settings are selected by one or more users of the medical system, and
wherein the basic settings relating to representation manners for at least one of the one or more users are same across the plurality of different user interface devices independently of a specific operating system of any one of the plurality of different image user interface devices, and
wherein the instrument is one of a plurality of instruments that are connected to the user interface device, wherein the electromagnetic position acquisition apparatus is further configured to switch between acquisition of a position of any one of the plurality of instruments that are connected to the user interface device, and wherein the user interface device is configured to switch between displaying a representation of any one of the plurality of instruments that are connected to the user interface device.

2. The medical system of claim 1, wherein the computer is further configured to display in the body part a marking of a further position and/or target region or target volume in the body part.

3. The medical system of claim 1, wherein the user interface device is configured to display the view of the body part with a 1:1 scale.

4. The medical system of claim 1, wherein the computer is further configured to access different data representing the body part and to generate an image that is based on selected data from the accessed different data representing the body part, and wherein the one or more control elements of the user interface device permit a selection to be made between the accessed different data representing the body part, wherein the user interface device generates a control signal when one of the one or more control elements is actuated, and wherein the control signal causes the computer to generate the image on the basis of the selected data from the accessed different data representing the body part of a patient.

5. The medical system of claim 1, wherein the computer is further configured to store a currently displayed image in such a way that it can be recalled at a later time, wherein the user interface device comprises a control element of the one or more control elements and generates a control signal when the control element is actuated, and wherein the control signal causes the computer to store the currently displayed image when the control element is actuated.

6. The medical system of claim 1, wherein the user interface device is configured to indicate to the one or more users landmarks on multiple representations of the view of the body part, such that landmarks are aligned across the multiple representations.

7. The medical system of claim 1, wherein the user interface device is configured to display an endoscopic recording in a view generated from data obtained by tomography.

8. The medical system of claim 1, wherein the user interface device is configured to display an endoscopic recording in a view generated from data obtained by magnetic resonance imaging.

9. The medical system of claim 1, wherein the switching of the representation of any one of the plurality of instruments on the user interface device is performed automatically as a specific one of the plurality of instruments is moved by one of the one or more users.

10. The medical system of claim 1, wherein the user interface device is configured to modify a display of a control element of the one or more control elements to represent a respective instrument of the plurality of instruments is currently in use by one of the one or more users.

11. The medical system of claim 1, wherein the user interface device is further configured to focus attention on a plurality of image points or positions in a two-dimensional plane or a three-dimensional space, and wherein the plurality of image points or positions are stored on either the user interface device or the instrument, wherein the stored plurality of image points or positions are connected together to form a polygonal train defining a tissue shape or cavity in the view of the body part.

12. The medical system of claim 1, wherein the instrument is configured to continuously track position and alignment to generate a continuously recorded template defining a tissue shape or cavity in the view of the body part.

13. The medical system of claim 1, wherein the computer is configured to store an image sequence, wherein the user interface device comprises a control element of the one or more control elements and generates a control signal when the control element is actuated, and wherein the control signal causes the computer to record the image sequence.

14. The medical system of claim 13, wherein the user interface device is configured to generate a second control signal following a second actuation of the control element, and wherein the second control signal causes the computer to stop the recording of the image sequence.

15. The medical system of claim 13, wherein the user interface device is configured to modify a display of the control element for triggering the recording of the image sequence subsequent to actuation which starts the recording of the image sequence.

16. The medical system of claim 15, wherein the user interface device is configured to revert the display of the control element following a second actuation of the control element.

17. The medical system of claim 1, wherein the user interface device is further configured to receive input from one of the one or more users that marks or traces elements onto the view of the body part.

18. The medical system of claim 17, wherein the input is used to generate corresponding position data for the view of the body part.

19. The medical system of claim 17, wherein the input is used to generate landmarks on multiple representations of the view of the body part, wherein the landmarks are aligned across the multiple representations.

* * * * *